United States Patent [19]
Milavec et al.

[11] 4,239,763
[45] Dec. 16, 1980

[54] α-BLOCKING AGENTS IN THE TREATMENT OF OBESITY

[75] Inventors: Maria Milavec, St. Louis, France; Heribert Wagner, Pfeffingen, Switzerland

[73] Assignee: Sandoz Ltd., Basel, Switzerland

[21] Appl. No.: 51,055

[22] Filed: Jun. 22, 1979

Related U.S. Application Data

[63] Continuation of Ser. No. 952,380, Oct. 18, 1978, abandoned.

[30] Foreign Application Priority Data

Oct. 24, 1977 [GB] United Kingdom ............... 44147/77

[51] Int. Cl.³ ............................................. A61K 31/48
[52] U.S. Cl. .................................................. 424/261
[58] Field of Search .......................................... 424/261

[56] References Cited

U.S. PATENT DOCUMENTS

| 3,074,847 | 1/1963 | Bigsby | 424/261 |
|---|---|---|---|
| 3,652,569 | 3/1972 | Stadler et al. | 424/261 |
| 4,076,715 | 2/1978 | Fehr et al. | 424/261 |
| 4,122,177 | 10/1978 | Fehr | 424/261 |

FOREIGN PATENT DOCUMENTS 1180120  2/1970  United Kingdom ..................... 424/261

Primary Examiner—Douglas W. Robinson
Attorney, Agent, or Firm—Gerald D. Sharkin; Robert S. Honor; Thomas O. McGovern

[57] ABSTRACT

Alpha-blocking agents, especially 9,10-dihydroergotpeptide alkaloids, are anti-obesity agents.

4 Claims, No Drawings

α-BLOCKING AGENTS IN THE TREATMENT OF OBESITY

This is a continuation of application Ser. No. 952,380 filed Oct. 18, 1978, now abandoned.

The present invention relates to a new use of alpha blocking agents, particularly 9,10-dihydro-ergot-peptide alkaloids, especially compounds of formula I,

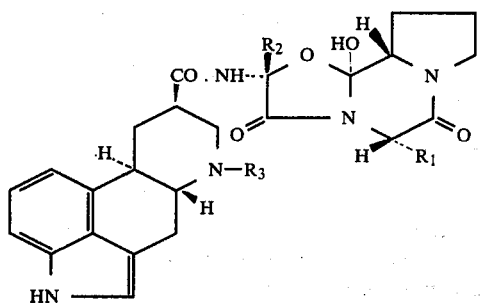

wherein
$R_1$ is isopropyl, isobutyl, sec. butyl or benzyl,
$R_2$ is methyl, ethyl or isopropyl and
$R_3$ is methyl or isopropyl.

Such compounds include dihydroergocornine, dihydroergocristine, dihydro-α-ergocryptine, dihydroergo-β-ergocryptine or mixtures of these four compounds, such as dihydroergotoxin; dihydroergotamine; dihydroergonine; 6-nor-6-isopropyl-dihydroergotamine, or 9,10-dihydro-2β methyl-5'α-isopropyl-6-nor-6-isopropyl-ergopeptine.

Other alpha-blocking agents, such as nicergoline, particularly those with little peripheral activity are also suitable.

It has now been found that these compounds are useful as for the reduction of obesity and reduction of body weight particularly when the fat cells have a preponderance of α-receptors as indicated by an increase of noradrenaline-stimulated lipolysis in isolated fat cells.

In one experiment, isolated fat cells from female patients and from rhesus monkeys were prepared according to the method of Rodbell [J.Biol.Chem.239, 375–380 (1964)]. Noradrenaline (concentration $10^{-6}$ to $10^{-7}$ Molar) was added to a fat cell suspension of 30 mg fat cells per ml and incubated in the presence of air for 2 hours. The glycerol release was used as an index of lipolysis and was in the range of 0.4 to 0.5 μmoles/-mmole triglycerides/hour. When the noradrenaline was added in the presence of $10^{-7}$ to $10^{-9}$ molar solution of the compound the glycerol release increased, e.g. to 3.9 μmole/mmole triglycerides/per hour.

The effect can also be observed in standard clinical trials. For example administration of 7 to 30 mg daily of the compound to an obese hyperlipidemic subject leads over one month to a rise of cholesterol and free fatty acid levels as well as to a reduction of body weight.

Dihydroergotamine and especially dihydroergotoxine have exhibited particularly interesting activity.

For the anti-obesity use the dosage will, of course, vary depending on the compound employed, mode of administration and treatment desired. However, in general, satisfactory results are obtained when administered at a daily dosage of from about 0.0001 mg to about 1 mg per kg animal body weight, conveniently given in divided doses 2 to 4 times a day or in sustained release form. For the larger mammals, the total daily dosage is in the range from about 0.1 to about 30 mg, and dosage forms suitable for oral administration comprise from about 0.02 mg to about 15 mg of the compounds admixed with a solid or liquid pharmaceutical carrier or diluent.

The compound may be administered in free base form or in pharmaceutically acceptable acid addition salt form, e.g. the hydrochloride or mesylate.

The compound may be administered orally in the form of tablets, powders, granules, capsules, suspensions, sirups and elixirs, or parenterally in the form of injectable solutions or suspensions. Oral administration is preferred. Aside from the compound the preparations may contain pharmaceutically inert organic or inorganic adjuvants, optionally granulating agents, binding agents, lubricants, dispersing agents, wetting agents and preservatives. Moreover, the pharmaceutical preparations may contain colouring, flavouring and sweetening substances, etc. Adjuvants for the production of tablets may be calcium carbonate, lactose, microcrystalline cellulose, mannitol or talc. Starch and alginic acid or microcrystalline cellulose may be used as granulating and disintegrating agents, starch, polyvinylpyrrolidone and gelatine may be used as binding agents, and magnesium stearate, stearic acid and talc as lubricants. Tablet formulations may be coated. Suitable suspending agents for the production of liquid administration forms are especially methyl cellulose, tragacanth and sodium alginate. Suitable wetting agents are e.g. polyoxyethylene stearate and polyoxyethylene sorbitan-monooleate. Furthermore, preservatives such as p-hydroxy-benzoic acid alkyl ester may be used. Capsule formulations may contain the compound on its own or together with an inert solid diluent, for example calcium phosphate, starch, lactose, mannitol, and microcrystalline cellulose.

Solid preparations are preferred, especially hardfilled capsules and tablets, for reasons of easier production and favourable administration.

Conveniently the compounds are administered in the absernce of other pharmacologically agents. Conveniently the compounds may be administered in conjunction with a slimming diet or low calorie diet, e.g. of up to 1,000 calories per day.

In one example, the compounds are administered to young subjects, conveniently of biological age from about 10 to 45 or 10 to 35.

It will be appreciated that the compounds are known pharmaceuticals. For example dihydroergotoxine is used for the treatment, inter alia, of cerebral insufficiency, functional and obliterative peripheral vascular disorders, migraine, hypertension, and cervical syndromes. Dihydroergotamine has been used for the treatment and prevention of attacks of vascular headaches and the treatment of meteropathological syndromes, side effects of sympathonic origin arising from treatment with thymoleptics and transquillisers, post-operative retention of urine, neurocirculatory dystonia, orthostatic hypotonia, herpes zoster, herpes labialis and genitalis, and herpetic diseases of the eye. The other above-mentioned compounds have been proposed for the treatment of at least one of these aforementioned conditions.

The above compounds have also been proposed for use in the treatment of the sickle-cell anaemia, oligiospermia and asthenospermia.

By way of example the following compositions may be used in the method of the invention.

EXAMPLE 1

Dihydroergotamine tablets

Each tablet contains:
Dihydroergotamine mesylate: 1.015 mg
Tartaric acid: 0.1 mg
Lactose (pulverized): 84.985 mg
Corn starch: 8.00 mg
Gelatine: 0.3 mg
Magnesium stearate: 0.5 mg
Stearic acid: 1.1 mg
Talc: 4 mg

EXAMPLE 2

Dihydroergotoxin tablets

Each tablet contains:
Dihydroergotoxin mesylate: 1.015 mg
Stearic acid: 2 mg
Polyvinylpyrrolidone: 4 mg
Talc: 4 mg
Corn starch: 8 mg
Lactose: 140.985 mg If desired tablets may be made with 0.25 mg or 15 mg of dihydroergotoxin mesylate in analogous manner.

The above-mentioned tablets are useful in the treatment of obesity when administered 3 to 5 times a day.

What we claim is:

1. A method of treating obesity or reducing body weight in animals in need of such treatment which comprises administering to said animals a therapeutically effective amount of a 9,10-dihydro-ergot-peptide of the formula

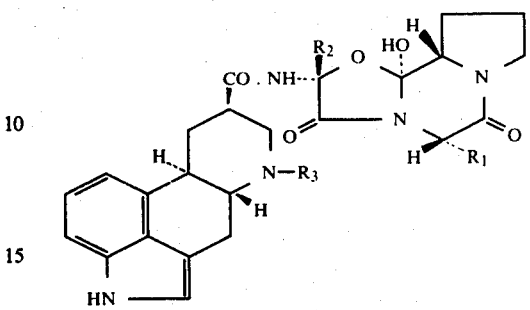

wherein
$R_1$ is isopropyl, isobutyl, sec. butyl or benzyl,
$R_2$ is methyl, ethyl or isopropyl and
$R_3$ is methyl or isopropyl.

2. A method of claim 1 wherein the compound is dihydroergotamine or dihydroergotoxine.

3. A method of claim 1 wherein the compound is administered in unit dosage form containing from about 0.02 mg to about 15 mg.

4. A method of claim 1 wherein the compound is administered in conjunction with a low calorie or slimming diet.

* * * * *